United States Patent [19]

Fuller et al.

[11] Patent Number: 5,010,080
[45] Date of Patent: Apr. 23, 1991

[54] USE OF HETEROCYCLIC AMIDES TO INHIBIT TUMOR METASTASIS

[75] Inventors: George C. Fuller, Gross Point, Mich.; George R. Martin, Bethesda, Md.; Richard A. Mueller, Glencoe, Ill.; Reuven Reich, Silver Spring, Md.

[73] Assignees: G. D. Searle & Co., Chicago, Ill.; The United States of America as represented by the Department of Health and Human Services, Washington, D.C.

[21] Appl. No.: 279,584

[22] Filed: Dec. 2, 1988

[51] Int. Cl.$^5$ .............................................. A61L 31/495
[52] U.S. Cl. ..................................................... 514/255
[58] Field of Search ........................................ 514/255

[56] References Cited

U.S. PATENT DOCUMENTS

| | | | |
|---|---|---|---|
| 4,029,812 | 7/1972 | Wagner et al. | 260/500.5 H |
| 4,076,841 | 6/1978 | Wagner et al. | 260/559 T |
| 4,078,084 | 4/1978 | Wagner et al. | 260/500.5 H |

FOREIGN PATENT DOCUMENTS

| | | | |
|---|---|---|---|
| 86101300.1 | 4/1986 | European Pat. Off. | |
| 0190685 | 8/1986 | European Pat. Off. | 514/255 |

OTHER PUBLICATIONS

Albini, A., et al., Cancer Research, 47:3239–3245, (1987).
Anderson, et al., The Prostate 12:3–12, (1988).
Black, K. L., et al., Annals of Neurology 19(6):592–595, (1986).
Dano, et al., Adv. Cancer Res. 44:139–266, (1985).
Fidler, I. J., et al., Adv. Cancer Res. 28:149–250, (1978).
Honn, et al., Biochem. Biophys. Res. Commun. 102:1122, (1981).
Honn, et al., Science 212:1270, (1981).
Hujanen, E. S., et al., Cancer Research 45:3517–3521, (1985).
Liotta, L. A., Am. J. Pathology 117:339–348, (1986).
McCarthy, J. B., et al., Cancer Metastasis Rev. 4:125–152, (1985).
Martin, G. R., et al., Ann. Rev. Cell Biol. 3:57–85, (1987).
Murphy, G., et al., Biochem Biophys Acta 831:49–58, (1985).
Nakajima, M., et al., Cancer Research 47:4869–4876, (1987).
Nardone, et al., J. Surg. Res. 44(4):425–429, (1988).
Reich, R., et al., Cancer Res. 48:3307–3312, (1988).
Terranova, V. P., et al., J. Natl. Cancer Inst. 77:311–316, (1986).
Fischer, S. M., et al., Adv. Prostaglandin, Thromboxane, Leukotriene Res., 12: 309 (1983).
Honn, et al., Adv. Prostaglandin Thromboxane, Leukotriene Res. 12: 313, (1983).

Primary Examiner—Jerome D. Goldberg
Attorney, Agent, or Firm—Mary Jo Kanady; Paul D. Matukaitis

[57] ABSTRACT

A method of inhibiting tumor metastasis in an animal without treating the tumor cells by administering to said animal a metastasis inhibiting effective amount of a heterocyclic amide represented by the formula:

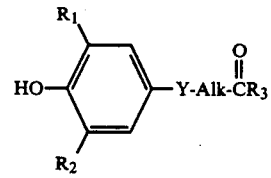

wherein: $R_1$ and $R_2$ are the same or different members of the group consisting of halo, phenyl, substituted phenyl and a

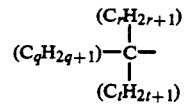

group wherein q, r and t are independently an integer of from 1 to 8 provided that $q+r+t$ is equal to or less than 10; Y is thio or sulfinyl; alk is straight or branched chain lower alkylene, and $R_3$ is a heterocyclic amine represented by the formula:

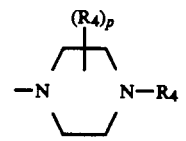

wherein $R_4$ is selected from the group consisting of hydrogen, lower alkyl, phenyl, substituted phenyl, benzyl, or substituted benzyl; p is 0 to 2; or a pharmaceutically acceptable salt thereof.

6 Claims, No Drawings

USE OF HETEROCYCLIC AMIDES TO INHIBIT TUMOR METASTASIS

The present invention relates to the use of heterocyclic amides; and more particularly, heterocyclic amides which are basic, specific 5-lipoxygenase inhibitors, to inhibit tumor metastasis without treating the tumor cells.

BACKGROUND OF THE INVENTION

It is generally understood that the metastasis of tumor cells is a critical event in the natural history and spread of cancer The spread of the tumor often places it beyond surgical treatment and results in a drastically worsened prognosis for the patient. Current concepts suggest that metastasis is a complex, multistep process (Fidler, I. J. et. al., *Adv. Cancer Res.*, 28: 149–250, 1978). However, invasion through basement membrane is an essential step in the process by which tumor cells form new lesions and this may involve a common mechanism for many tumor cells. Basement membranes (Martin, G. R., et. al., *Ann. Rev. Cell Biol.*, 3: 57–85, 1987), are the extracellular structures surrounding most epithelial tissues, nerves and muscle and lining most blood and lymph vessels. Collagen IV, laminin and a large heparan sulfate proteoglycan are major components of basement membranes. Basement membranes represent significant barriers to most cells, but malignant tumor cells can penetrate them. This is believed to require degradation by specific proteolytic enzymes (Liotta, L. A., *Am. J. Pathology*, 117: 335–348, 1986), (Terranova, V. P. et. al., *J. Natl. Cancer Inst.*, 77: 311–316, 1986). Because the basement membranes in all tissues have the same components, (Martin, G. R., et. al., *Ann. Rev. Cell Biol.*, 3: 57–85, 1987), it is possible that similar mechanisms are employed by many malignant tumor cells in invading basement membranes, although this has not been shown directly. The degradation of the collagen IV network may be the critical step, (Liotta, L. A., *Am. J. Pathology*, 117: 335–348, 1986), (Terranova, V. P. et al., *J. Natl. Cancer Inst.*, 77: 311–316, 1986) and it may be possible that collagenase IV is needed to do this. However, this is uncertain since other proteases includinq gelatinase, stromelysin, and elastase are able to degrade the collagen IV monomer under in vitro conditions (Murphy, G. et. al., *Biochem. Biophys. Acta*, 831: 49–58, 1985).

Collagenase IV is secreted in an inactive form. Activation of the enzyme is achieved via plasminogen activator and plasmin. Inhibition of either enzyme prevents malignant tumor cells from being invasive (Reich, R. et. al., Cancer Res. 48: 3307–3312, 1988). A high production of plasminogen activator is frequently observed with malignant cells (Dano, et. al., *Adv. Can. Res.* 44: 139–266, 1985).

Laminin and the protein of the heparan sulfate proteoglycan are susceptible to a variety of proteolytic enzymes. Degradation of the heparan sulfate chains requires a heparanase, and inhibitors of this enzyme have been shown to be antimetastatic in experimental studies (Nakajima, M., et. al., *Cancer Research*, 47: 4869–4876, 1987).

Motility factors and tissue chemotactic factors can stimulate the movement of malignant tumor cells and have been implicated in the organ specific metastasis of certain tumor cells (Hujanen, E. S. et. al., *Cancer Research*, 45: 3517–3521, 1985). Matrix proteins such as laminin have both chemotactic and heptotactic activity and might be expected to accelerate the movement of malignant tumor cells (McCarthy, J. B. et. al., *Cancer Metastasis Rev.*, 4: 125–152, 1985). In vitro assays of tumor cell invasiveness often employ chemoattractants to increase the migration of the tumor cells (Albini, A. et. al., *Cancer Research*, 47: 3239–3245, 1987). Chemoattractants may have a significant role in tumor cell metastasis.

Hematogenous tumor metastasis is thought to be mediated in part by alternations in vascular integrity and interactions with platelets. Arachidonic acid metabolites, i.e., prostacyclin, thromaoxane $A_2$ and leukotrienes are powerful modulators of vascular integrity, tone and platelet aggregation and may be involved in the development of tumor growth and metastasis. There is evidence of a correlation between tissue levels of leukotriene $C_4$ levels and vasogenic edema surrounding brain tumors, K. C. Black, et al. ANNALS OF NEUROLOGY 19(6):592–595 (1986). Honn, et al., demonstrated that selective inhibition of thromboxane synthetase, as well as pretreatment with exogenous prostacyclin significantly decreased hematogenous metastases in animal models. SCIENCE 212:1270(1981); ADV.-PROSTAGLANDIN, THROMBOXANE, LEUKOTRIENE RES.12:313 (1983); BIOCHEM. BIOPHYS. RES. COMMUN. 102:1122(1981). Ketoconazole, an antifungal agent which inhibits both the thromboxane synthetase and 5-lipoxygenase metabolic pathways significantly reduced metastasis of B16-F10 murine melanoma cells in mice, P. A. Wardone, et. al, J. SURG. RES. 44 (4): 425–429 (1988). When human PC-3 cells derived from a metastatic prostate adenocarcinoma were incubated with eicosatetraynoic acid, an in vitro inhibitor of arachidonic acid metabolism (cyclooxygenase and lipoxygenase), DNA synthesis was supressed, K. M. Anderson, et al., THE PROSTATE 12:3–12 (1988).

Cyclooxygenase inhibitors have been used as nonsteroidal antiinflammatory agents (NSAID's) and analgesics. Mixed cyclooxygenase/lipoxygenase inhibitors such as benoxaprofen have been used for the same purposes. Both groups of drugs have exhibited undesirable toxicity in human use (see for example, Goodman and Gilman, *The Pharamcoloqical Basis of Therapeutics*, Seventh Ed. (1985) Chapter 29 pages 674–715).

Wagner, et al., U.S. Pat. No. 4,029,812, and related U.S. Pat. Nos. 4,076,841 and 4,078,084 which issued from divisional applications of the -812 application, all assigned to The Dow Chemical Company, disclose 2-(3,5-di-tert-butyl-4-hydroxyphenyl) thiocarboxylic acids, esters and simple amides which are hypolipidemics and are useful in reducing plasma lipid levels, especially cholesterol and triglyceride levels.

European Patent Application No. 86 101 300.1 discloses 5-lipoxygenase inhibiting compounds which are useful as anti-inflammatory and anti allergy agents and which are represented by the formula

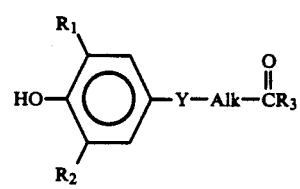

wherein $R_1$ and $R_2$ are the same or different members of the group consisting of halo, phenyl, substituted phenyl and a

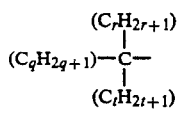

group wherein q, r and t are independently an integer of from 1 to 8 provided that $q+r+t$ is equal to or less than 10; Y is thio, sulfinyl or sulfonyl; Alk is straight or branched chain lower alkylene, and $R_3$ is a heterocyclic amine represented by the formula:

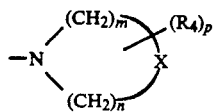

wherein $R^4$ is selected from the group consisting of hydrogen, lower alkyl, phenyl, substituted phenyl, benzyl, substituted benzyl, carboxyl or carboxylower alkyl; X is selected from the group consisting of N—$R_4$, O and $CH_2$; m is 2 or 3; n is 2 or 3 when X is O or N—$R_4$ and n is 1 to 3 when X is $CH_2$; p is 0 to 2; and the pharmaceutically acceptable salts thereof.

SUMMARY OF THE INVENTION

The present invention relates to a method of inhibiting tumor metastasis in an animal without treating the tumor cells by administering to an animal in need of such treatment an amount of a heterocyclic amide represented by the formula I

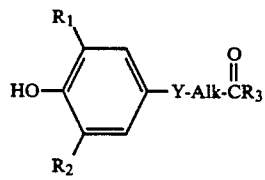

wherein: $R_1$ and $R_2$ are the same or different members of the group consisting of halo, phenyl, substituted phenyl and a

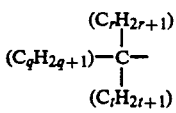

group wherein q, r and t are independently an integer of from 1 to 8 provided that $q+r+t$ is equal to or less than 10; y is thio or sulfinyl; Alk is straight or branched chain lower alkylene, and $R_3$ is a heterocyclic amine represented by the formula:

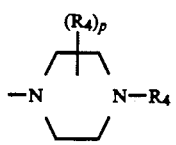

wherein $R_4$ is selected from the group consisting of hydrogen, lower alkyl, phenyl, substituted phenyl, benzyl, or substituted benzyl; p is 0 to 2; or a pharmaceutically acceptable salt thereof, effective to inhibit tumor metastasis.

These compounds are chemically basic, selective 5-lipoxygenase inhibitors which have unexpectedly been found to be useful in inhibiting the metastasis of tumors in animals and thereby decreasing tumor burden. Not all specific 5-lipoxygenase inhibitors are effective; for example, acidic compounds do not appear to be active in inhibiting metastasis.

Representative heterocyclic amines include, but are not limited to piperazine, 4-(phenylmethyl)piperazine, 4-methylpiperazine, 2-methylpiperazine and the like.

The present invention also includes pharmaceutical compositions comprising a tumor metastasis inhibiting effective amount of a compound of formula I in unit dosage form along with a pharmaceutically acceptable carrier.

DETAILED DESCRIPTION OF PREFERRED EMBODIMENTS

The present invention relates to a method of inhibiting tumor metastasis in an animal by administering to an animal in need of such treatment a therapeutically effective tumor metastasis inhibiting amount of a compound of the formula

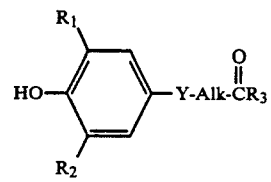

wherein: $R_1$ and $R_2$ are the same or different members of the group consisting of halo, phenyl, substituted phenyl and a

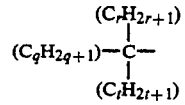

group wherein q, r and t are independently an integer of from 1 to 8 provided that $q+r+t$ is equal to or less than 10; Y is thio or sulfinyl; Alk is straight or branched chain lower alkylene, and $R_3$ is a heterocyclic amine represented by the formula I:

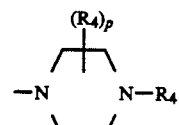

wherein $R_4$ is selected from the group consisting of hydrogen, lower alkyl, phenyl, substituted phenyl, benzyl, or substituted benzyl; p is 0 to 2; or a pharmaceutically acceptable salt thereof.

Preferred compounds for use in inhibiting tumor metastasis in animals are compounds of the formula

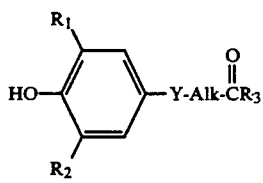

wherein: $R_1$ and $R_2$ are the same or different and are a

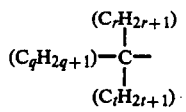

group wherein q, r and t are independently an integer of from 1 to 8 provided that $q+r+t$ is equal to or less than 10; Y is thio or sulfinyl; Alk is straight or branched chain lower alkylene, and $R_3$ is a heterocyclic amine represented by the formula:

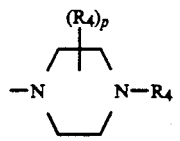

wherein $R_4$ is selected from the group consisting of hydrogen, lower alkyl, phenyl, substituted phenyl, benzyl, or substituted benzyl; p is 0 to 2; or a pharmaceutically acceptable salt thereof.

Especially preferred compounds for use in inhibiting tumor metastasis in animals are compounds of the formula

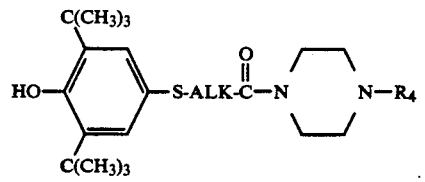

wherein Alk is straight or branched chain lower alkylene and $R_4$ is selected from the group consisting of hydrogen, lower alkyl, phenyl, substituted phenyl, benzyl, or substituted benzyl; or a pharmaceutically acceptable salt thereof.

A particularly preferred compound for use in inhibiting tumor metastasis in an animal is a compound of the formula

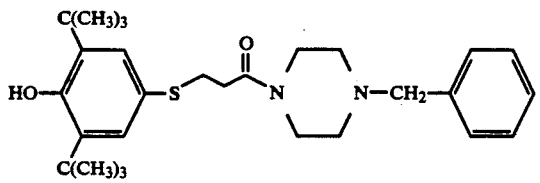

or a pharmaceutically acceptable salt thereof.

Generally speaking, synthesis of the compounds used in this invention is accomplished by displacement of the halogen or tosylate on a halo or tosyl substituted aliphatic acyl heterocyclic amide by a thiol in the presence of a base. Addition of a thiol to the double bond of any alkenyl acyl heterocyclic amide is also an useful synthetic route. Alternatively, the displacement, via reaction with a thiol and base, can be carried out on a tosyl or halo substituted aliphatic carboxylic acid or ester which is then converted into the amide via reaction of the corresponding acid chloride with the desired heterocyclic amine. An ester is preferably hydrolyzed to the corresponding acid before conversion to the acid chloride by, for example, oxalyl chloride. The sulfones and sulfoxides are readily prepared by oxidation of a sulfide with for example, m chlorobenzoic acid or sodium metaperiodate.

The term "lower alkyl", as used herein, refers to straight or branched chain alkyl groups having from 1 to 6 carbon atoms, inclusive, i.e., methyl, ethyl, n-propyl, iso-propyl, n-butyl, sec-butyl, tert-butyl, n-pentyl, 2-methylbutyl, 2,2-dimethylbutyl, n-hexyl, and the like.

The term "lower alkylene", as used herein, refers to straight or branched chain lower alkylene groups having from 1 to 6 carbon atoms, i.e., methylene, ethylene, n-propylene, iso-propylene, n-butylene, sec-butylene, tert-butylene, 3-methylpentylene, 2-methylbutylene, 1,1-dimethylethylene, and the like.

The term "halo", as used herein, includes chloro, bromo, iodo and fluoro.

The term "substituted phenyl" refers to phenyl having one or more substituents selected from the group consisting of amino, halo, hydroxy, lower alkyl, lower alkylaminoalkyl, lower dialkylaminoalkyl, trifluoromethyl, lower alkoxy, and the like for $R_4$ and halo, hydroxy, lower alkyl and lower alkoxy for $R_1$ and $R_2$.

The term "lower alkoxy" refers to alkoxy groups having from 1 to 6 straight or branched chain carbon atoms, i.e., methoxy, ethoxy, n-propoxy, tert-butoxy, etc.

The term "substituted benzyl" refers to benzyl groups having one or more substituents selected from the group consisting of halo, hydroxy, lower alkyl and lower alkoxy.

The term "pharmaceutically acceptable salt" refers to the physiologically acceptable acid addition salts of the amides of the present invention prepared by treating the compound with an appropriate acid as is well known in the art. Such salts include, but are not limited to, the hydrochloride, hydrobromide, sulfate, maleate, napsylate, oleate, succinate, palmitate, laureate, fumarate, phosphate, acetate, tartrate, stearate, nitrate, citrate, tosylate and like salts.

Preferred radicals represented by the group of the formula

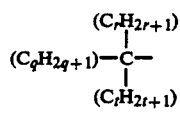

include tertiary alkyl moieties wherein q and r are preferably 1 or 2 and most preferred radical is represented by the group wherein q, r and t are 1, namely t-butyl. The groups represented by Y are preferably thio and sulfinyl, and most preferably thio.

The metastasis inhibiting activity of the compounds of this invention was first determined using the assay described in R. Reich, et al., "Effects of Inhibitors of Plasminogen Activator, Serine Proteases and Collagenase IV on the Invasion of Basement Membranes by Metastastic Cells in Mice and Humans," CANCER RESEARCH 48: 3307-3312 (1988) and Albini, A., et al., "A rapid in vitro assay for quantitating the invasive potential of tumor cells" CANCER RES. 47: 3239-3245 (1987).

Chemoinvasion and Chemotaxis Assays

The chemoinvasion assay was performed as previously described by Albini, et al. Briefly, polyvinylpyrrolidone-free polycarbonate filters, 8-μ pore size (Nucleopore CA) were coated with an extract of basement membrane components (Matrigel, 25 μg/filter, i.e., 0.5 μg/mm²) and placed in modified Boyden chambers. This amount of Matrigel forms an even coating over the surface of the filter and the ultrastructure of the reconstituted basement membrane has been reported to resemble, in part, authentic basement membranes. Kleinman, H. K., et al., "Basement membrane complexes with biological activity," BIOCHEMISTRY, 25: 312-318 (1986). The cells to be studied ($2 \times 10^5$) were collected by short exposure to EDTA (1 mM) resuspended in 0.1% bovine serum albumin in Dulbecco's minimum essential medium and placed in the upper compartment of the Boyden chamber. Fibroblast conditioned media were placed in the lower compartment as a source of chemoattractants. The chemotactic assays were conducted in a similar fashion except with a small amount (5 μg/filter) of collagen IV instead of Matrigel. After incubation for 6 h at 37° C. the cells on the lower surface of the filter were stained and quantitated with an image analyzer (Optomax IV) attached to an Olympus CK2 microscope. The data are expressed as the area of the bottom surface of the filter occupied by cells and is proportional to the number of cells on this surface.

Results for certain compounds are shown in Table 1. Results are expressed as micrometers squared times $10^{-3}$.

TABLE 1

| INHIBITION OF THE INVASIVE ACTIVITY OF HT-1080 CELLS | | | | |
|---|---|---|---|---|
| | Concentration μM | | | |
| COMPOUND | 0 | 1 | 10 | 50 |
| EXAMPLE 4 | 108.8 | — | 74.39 | 41.43 |
| EXAMPLE 8 | 108.8 | — | 45.99 | 23.19 |

The following non-limiting examples further illustrate details for the preparation of compounds used in practicing the present invention. Those skilled in the art will readily understand and appreciate that known variations of the conditions and procedures in the following preparative methods can be utilized. All temperatures are degrees Celsius unless otherwise noted. Melting points were determined on a Thomas-Hoover melting point apparatus and are uncorrected.

The following examples further illustrate the present invention.

EXAMPLE 1

Preparation of 3,5-bis(1,1-dimethylethyl)-4-hydroxyphenylthiocyanate

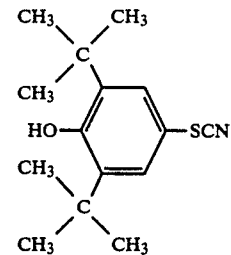

To a three-necked, round bottom 5 L flask, equipped with a mechanical stirrer, gas inlet, thermometer and gas inlet, thermometer and gas outlet, was added 2,6-di-tert-butylphenol (474 g, 2.30 mole), ammonium thiocyanate (76.12 g, 4.83 mole) and methanol (1200 ml). The reaction mixture was stirred and cooled to 0° C. in an ice/salt bath. Maintaining the temperature at 0° to 10° C., chlorine gas was slowly bubbled through the mixture for about 1 hour whereupon the reaction mixture was a heterogeneous yellow color. Ammonia was then bubbled through the reaction for about 1½ hours, maintaining the reaction mixture at a temperature of between 0° to 10° C. The reaction was stirred for an additional hour at 0° C., poured into a 2 L of cold distilled water and refrigerated overnight. The aqueous phase was decanted and the solid taken up in methanol, precipitated from water, filtered and dried for 2 days over phosphorous pentoxide. The resulting gummy yellow solid was recrystallized from pentane and dried in vacuo to yield the product as a white powder, m.p. 61.5°-63° C.

Analysis calc. for $C_{15}H_{21}NSO$:
Theory: C, 68.40; H, 8.03; N, 5.32; S, 12.17.
Found: C, 68.85; H, 8.05; N, 5.29; S, 12.12.

EXAMPLE 2

Preparation of 2,6-bis(1,1-dimethylethyl)-4-mercaptophenol

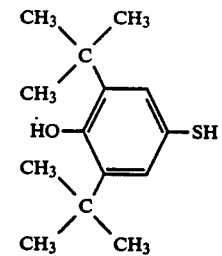

3,5-bis(1,1-Dimethylethyl)-4-hydroxyphenyl thiocyanate (55 g, 0.209 mole) was dissolved in acetone (200 ml) under an argon atmosphere. Water (7.6 g, 0.42 mole) was added and the reaction cooled to 0° C. Triethylphosphine (24.7 g, 0.209 mole) was added dropwise over a period of 1 hour and the reaction was then allowed to warm to room temperature with stirring. The solution was concentrated, solvents removed, and the resulting oil purified by chromatography on silica. The fractions containing the thiol were combined, the solvents removed to yield a white powder which was recrystallized from methanol/water and dried to yield 43.3 g of the desired product. NMR confirmed the identity of the product.

EXAMPLE 3

1-methyl-4-(1-oxo-2-propenyl)piperazine

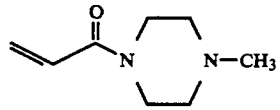

A solution of acryloyl chloride (9 g, 0.10 mole) in ethyl ether (20 ml) was added dropwise to a stirring, cold solution of N-methylpiperazine (10 g, 0.10 mole) and triethylamine (30.6 ml, 0.22 mole) in ethyl ether (150 ml) over a thirty minute period. An additional 75 ml of ethyl ether was added and the reaction stirred for 72 hours. The resulting white solid was filtered and washed well with ethyl ether. The ethyl ether was collected, combined with the filtrate and the solvent evaporated on a rotary evaporator to yield 9.5 g of product as an orange oil. NMR confirmed the structure of the product.

EXAMPLE 4

Preparation of 1-[3-[3,5-bis(1,1-dimethylethyl)-4-hydroxyphenyl]thio]-1-oxopropyl]-4-methylpiperazine

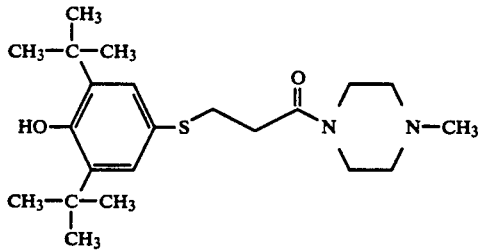

2,6-bis(1,1-dimethylethyl)-4-mercaptophenol (2.15 g, 0.009 mole) and 1-methyl-4-(1-oxo-2-propenyl)piperazine (1.39 g, 0.009 mole) were dissolved in methanol (75 ml). Triethylamine (1.5 ml) was added and the reaction stirred at room temperature for twelve hours. The solvent and triethylamine were removed on a rotary evaporator to give an oil. The product was purified by chromatography on silica gel, eluting with hexane/ethyl acetate. The resulting product (0.68 g) was dried in a vacuum pistol for 72 hours under an ethyl acetate reflux.

Elemental Analysis for $C_{22}H_{36}N_2O_2S$ (392.6):
Calc.: C, 67.30; H, 9.24; N, 7.14; S, 8.17.
Found: C, 67.42; H, 9.24; N, 7.05; S, 8.30.

EXAMPLE 5

Preparation of 1-[3-[3,5-bis(1,1-dimethylethyl-4hydroxyphenyl]thio]-1-oxopropyl]-4-methylpiperazine monohydrochloride

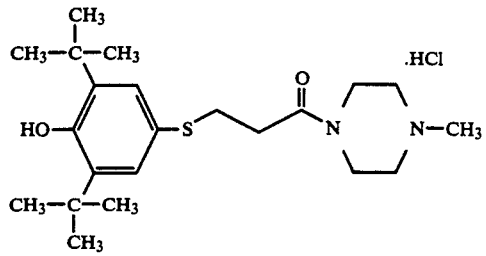

Following the procedure of Example 4, 2,6-bis-(1,1,-dimethylethyl)-4-thiophenol (1.19 g, 0.005 mole), 1-methyl-4-(1-oxo-2-propenyl)piperazine and triethylamine (0.5 ml) were combined and reacted for twelve hours. The solvents were removed under a nitrogen stream and the reaction chromatographed on silica. The product was collected, the solvents evaporated under a nitrogen stream and the resulting oil taken up in ethyl ether and a saturated hydrogen chloride-isopropanol solution added dropwise. After stirring for 12 hours, the hydrochloride salt as a white solid was filtered to yield 1.3 g of product. The product was dried in vacuo. m.p. about 201°–203° C. (429.05).

Elemental analysis for $C_{22}H_{37}N_2O_2SCl$ (429.06):
Calc.: C, 61.59; H, 8.69; Cl, 8.26; N, 6.53; S, 7.47.
Found: C, 61.83; H, 8.56; Cl, 8.50; N, 6.52; S, 7.49.

EXAMPLE 6

1-(1-oxo-2-propenyl)-4-(phenylmethyl)piperazine

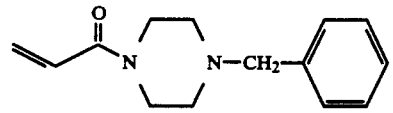

A solution of acryloyl chloride (4.52 g, 0.05 mole) in 25 ml of ethyl ether was added to a cold solution of 1-benzylpiperazine (8.8 g, 0.05 mole) and triethylamine (30 ml, 0.20 mole) in 500 ml of ethyl ether. A white precipitate formed. The reaction mixture was stirred overnight, filtered and the precipitate washed well with ethyl ether. The solvent and triethylamine were removed and the product chromatographed on silica, eluting with ethyl acetate/hexane [30:70 (v/v)] to yield 1.5 g of the title compound. The structure was confirmed by NMR.

EXAMPLE 7

Preparation of 1-[3-[[3,5-bis(1,1-dimethylethyl) 4-hydroxyphenyl]thio]-1-oxopropyl]-4-(phenylmethyl) piperazine

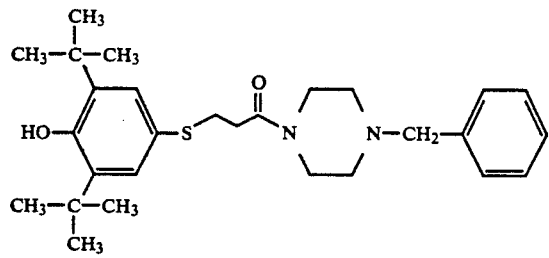

Following the method of Example 4, 2,6-bis-(1,1-dimethylethyl)-4-mercaptophenol (1.52 g, 0.0064 mole), 1-(1-oxo-2-propenyl)-4-phenylmethyl)piperazine (1.47 g, 0.0064 mole) and triethylamine (0.5 ml) were dissolved in 150 ml of methanol and stirred at room temperature for 12 hours. The solvent was removed on a rotary evaporator, and the reaction chromatographed on silica gel. The product was recrystallized from ethyl acetate and hexane. The resulting white solid was filtered and dried overnight in a vacuum pistol at room temperature, m.p. about 92.5°-95° C., (468.70).

Analysis calc. for $C_{28}H_{40}N_2SO_2$:

Calc.: C, 71.75; H, 8.60; N, 5.98; S, 6.84.

Found: C, 71.67; H, 8.69; N, 6.04; S, 6.87.

EXAMPLE 8

Preparation of 1-[3-[[3,5-bis(1,1-dimethylethyl)-4-hydroxyphenyl]thio]-1-oxopropyl]-4-(phenylmethyl)-piperazine monohydrochloride

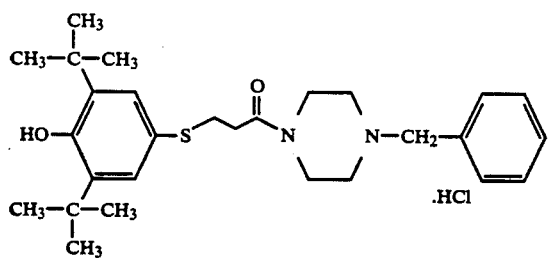

1-[3-[[3,5-bis(1,1-dimethylethyl)-4-hydroxyphenyl]-thio]-1-oxopropyl]-4-(phenylmethyl)piperazine (2.0 g) was dissolved in 700 ml of ethyl ether. A saturated solution of hydrogen chloride in isopropanol was added dropwise with rapid stirring, and the reaction stirred for 12 hours. The hydrochloride salt formed as a white solid which was filtered, and air dried to yield 2.05 g of product, m.p. ca. 214°-216.5° C.

Analysis calc for $C_{28}H_{41}N_2O_2ClS$ (505.16):

Cald.: C, 66.57; H, 8.18; Cl, 7.02; N, 5.55; S, 6.35.

Found: C, 66.54; H, 8.14; Cl, 7.39; N, 5.50; S, 6.50.

EXAMPLE 9

Preparation of 2'-hydroxy[1,1':3',1''-terphenyl]-5'-yl thiocyanate

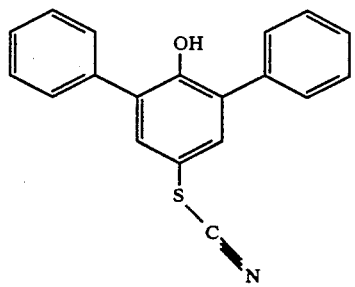

2,6,-Diphenylphenol (100.0 g, 0.406 mole) and ammonium thiocyanate (67.99 g, 0.893 mole) were suspended in methanol (150 ml) in a three necked round bottom flask equipped with magnetic stirrer, thermometer and bubbler. The reaction mixture was cooled to −5° C. in an acetone/ice bath and chlorine gas bubbled through the solution for three hours. Maintaining the temperature below 10° C., ammonia gas was bubbled through the reaction for 2 hours. The contents of the flask were then poured into iced distilled water (250 ml) and allowed to stand for 12 hours in the refrigerator. After filtering, the solid was dried in vacuo at 45° C. for 12 hours. The title compound was purified by chromatography on silica and recrystallized from hexane, m.p. about 104°-106.5° C.

Analysis calc. for $C_{19}H_{13}OSN$ (303.39):

Calc C, 75.22; H, 4.32; N, 4.62; S, 10.57.

Found: C, 75 12; H, 4.49; N, 4.65; S, 10.41.

EXAMPLE 10

Preparation of 1-[3-[(2'-hydroxy[1,1':3',1''-terphenyl]-5'-yl)thio]-1-oxopropyl]-4-(phenylmethyl)piperazine

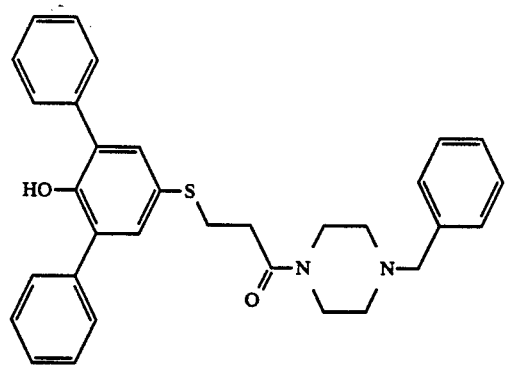

Following the procedure of Example 4, 1-(1-oxo-2-propenyl-4-phenylmethyl)piperazine (Example 6) (2.30 g, 0.01 mole) was dissolved in methanol (150 ml) and triethylamine (1 ml) added to the solution. The solution was flushed with argon several times, 5'-mercapto [1,1':3',1''-terphenyl]-2'-ol (2.77 g, 0.01 mole) added and the reaction stirred for 12 hours. The solvent was removed and the product isolated by chromatography to yield 1.5 g of product after drying in vacuo.

Analysis calc. for $C_{32}H_{32}N_2O_2S + 0.25\ C_4H_8O_2$:

Calc. C, 74.70; H, 6.46; N, 5.28; S, 6.04.

Found: C, 74.75; H, 6.21; N, 5.51; S, 6.22.

EXAMPLE 11

Preparation of 3,5-dichloro-4-hydroxyphenyl thiocyanate

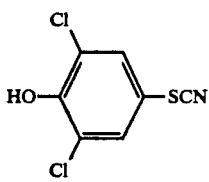

2,6-Dichlorophenol (100 g, 0.613 mole) and ammonium thiocyanate (102.73 g, 1.350 mole) were mixed in methanol and the solution cooled to 0° C. Chlorine gas was bubbled through the reaction, maintaining the temperature below 10° C. The solution turned a pale yellow color. The reaction was stirred for a total of 3 hours until acidic, at which time ammonia gas was bubbled through and the solution stirred for an additional three hours at 0° to 10° C. The reaction was poured into iced distilled water, and filtered, yielding approximately 20 g of a yellow solid which was dried overnight in vacuo. The filtrate was extracted with ethyl acetate, the extracts dried over magnesium sulfate and solvent removed in vacu to yield approximately 100 g of crude product. Following purification by silica chromatography, the material was taken up in 1 liter of toluene, charcoal added, filtered and recrystallized from hexane to yield 55.03 g of product as a yellow solid, m.p. about 94.5°–97° C. The structure was confirmed by NMR.

EXAMPLE 12

Preparation of 2,6-dichloro-4-mercaptophenol

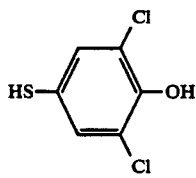

Following the method of Example 2, the title compound was prepared from 3,5-dicholoro-4-hydroxyphenyl thiocyanate. The structure was confirmed by NMR.

EXAMPLE 13

Preparation of 1-[3-[[3,5-dichloro-4-hydroxyphenyl]thio]-1-oxopropyl]-4-(phenylmethyl)piperazine

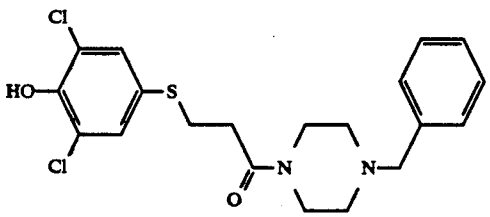

1-(1-Oxo-2-propenyl)-4-(phenylmethyl)piperazine (2.53 g, 0.011 mole) and 2,6-dichloro-4-mercaptophenol (2.15 g, 0.011 mole) were dissolved in methanol (75 ml). Triethylamine (1 ml) was added and the reaction stirred for 12 hours. The solvent was removed, and the product purified by chromatography on silica, eluting with ethyl acetate/hexane.

Analysis calc for $C_{20}H_{22}O_2N_2Cl_2S$:
Calc.: C, 56.47; H, 5.21; N, 6.59; Cl, 16.67; S, 7.54.
Found: C, 56.59; H, 5.35; N, 6.46; Cl, 16.71; S, 7.33.

EXAMPLES 14–17

By replacing 2,6-bis(1,1-dimethylethyl)-4-mercapto phenol with 2,6-dichloro-4-mercaptophenol in the procedure of Examples 4, 5, 7 and 8, the following compounds are obtained:

EXAMPLE 14

1-[3-[(3,5-dichloro-4-hydroxyphenyl)thio]-1-oxopropyl]-4-methylpiperazine.

EXAMPLE 15

1-[3-[(3,5-dichloro-4-hydroxyphenyl)thio]-1-oxopropyl-4-methylpiperazine monohydrochloride.

EXAMPLE 16

1-[3-[(3,5-dichloro-4-hydroxyphenyl)thio]-1-oxopropyl]-4-(phenylmethyl)piperazine.

EXAMPLE 17

1-[3-[(3,5-dichloro-4-hydroxyphenyl)thio]-1-oxopropyl]-4-(phenylmethyl)piperazine monohydrochloride.

EXAMPLES 18–21

By replacing 2,6-bis(1,1-dimethylethyl)-4-mercapto phenol with 5'-mercapto[1,1':3',1''-terphenyl]-2'-ol in Examples 4, 5, 7 and 8, the following compounds are obtained.

EXAMPLE 18

1-[3-[(2'-hydroxy[1,1':3',1''-terphenyl]-5'-yl)thio]-1-oxopropyl]-4-methylpiperazine.

EXAMPLE 19

1-[3-[(2'-hydroxy[1,1':3',1''-terphenyl]-5'-yl)thio]-1-oxopropyl]-4-methylpiperazine monohydrochloride.

EXAMPLE 20

1-[3-[(2'-hydroxy[1,1':3',1''-terphenyl]-5'-yl)thio]-1-oxopropyl]-4-(phenylmethyl)piperazine.

EXAMPLE 21

1-[3-[(2'-hydroxy[1,1':3',1''-terphenyl]-5'-yl)thio]-1-oxopropyl]-4-(phenylmethyl)piperazine monohydrochloride.

EXAMPLE 22

Preparation of 4-[[3,5-bis(1,1-dimethylethyl)-4-hydroxy phenyl]thio]butanoic acid

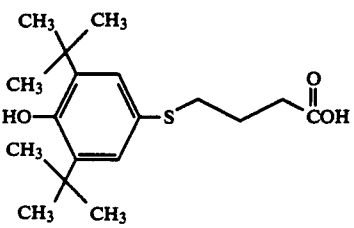

Potassium hydroxide flakes (2.52 g, 0.045 mole) were added to a clear solution of 2,6-bis(1,1-dimethylethyl)-4- mercaptophenol (3.57 g, 0.015 mole) and ethyl-4-bromobutyrate (3.23 g, 0.0165 mole) in acetone (10 ml). Water (20 ml) was added and the solution stirred for 1.5 hours, the solvent removed on a rotary evaporator and water (50 ml) added and extracted with ethyl ether (3×75 ml). The aqueous layer was acidified with concentrated hydrochloric acid, extracted with ethyl ether (2×50 ml), washed with water (50 ml), dried over sodium sulfate, filtered and the solvents removed, leaving an oil, which was purified by chromatography on silica, recrystallized from ethyl ether/Skellysolve B, filtered and the product dried in vacuo at room temperature for 12 hours, m.p. ca. 112°–113.5° C.

Analysis calc. for $C_{18}H_{28}O_3S$ (324.48):
Calc. C, 66.63; H, 8.70; S, 9.88.
Found: C, 66.71; H, 8.74; S, 9.57.

EXAMPLE 23

Preparation of
1-[4-[[3,5-bis(1,1-dimethylethyl)-4-hydroxy phenyl]thio]-1-oxobutyl]-4-(phenylmethyl)piperazine 4-[[3,5-bis(1,1-dimethylethyl)-4-hydroxyphenyl]thio]-butanoic acid is dissolved in benzene and the solution cooled to about 5° C. in an ice bath. A solution of oxalyl chloride in benzene is added dropwise over a period of about 5 minutes. The ice bath is removed and the solution is allowed to warm to room temperature and is stirred for about 5 hours. The benzene is evaporated and fresh benzene is added. Triethylamine and N-benzylpiperazine are added and the solution is stirred overnight. The benezene is evaporated on a rotary evaporator and the product is purified by chromatography on silica.

EXAMPLE 24

Preparation of 2-[[3,5-bis(1,1-dimethylethyl)-4-hydroxy phenyl]thio]pentanoic acid

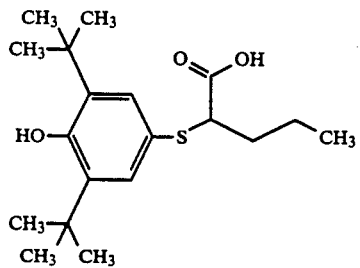

The title compound was prepared according to the method of Example 22 from potassium hydroxide flakes (3.36 g, 0.06 mole), 2,6-bis(1,1-dimethylethyl)-4-mercaptophenol (4.76 g, 0.02 mole) and ethyl-2-bromovalerate (4.18 g, 0.02 mole) in acetone (100 ml). The structure was confirmed by NMR.

EXAMPLE 25

Preparation of
1-[2-[[3,5-bis(1,1-dimethylethyl)-4-hydroxy phenyl]thio]-1-oxopentyl]-4-(phenylmethyl)piperazine The title compound of Example 24 is converted to its acid chloride and is reacted with N benzylpiperazine by the method of Example 23 to give the title compound.

EXAMPLE 26

Preparation of 2-chloro-N-(N-benzyl-piperazine)acetamide

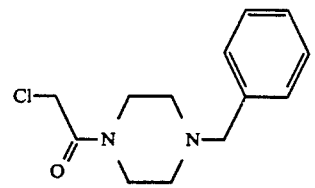

Chloroacetyl chloride in methylene chloride is cooled via an ice bath to 0° C. A solution of N-benzylpiperazine and triethylamine in methylene chloride is added dropwise over a period of 1 hour and the resulting solution stirred and allowed to come to room temperature during a 20 hour period. 10% Hydrochloric acid is added and the layers are separated. The organic layer is washed with 1N hydrochloric acid and water, is dried over sodium sulfate, filtered and the solvent is removed to give the title compound.

EXAMPLE 27

Preparation of
1-[2-[[3,5-bis(1,1-dimethylethyl)-4-hydroxy-phenyl]thio]-1-oxoethyl]-4-(phenylmethyl)lpiperazine

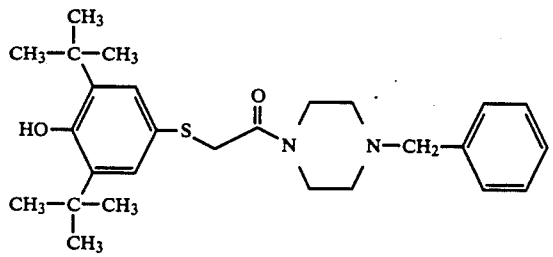

The title compound is prepared by dissolving the product of Example 26 and 2,6-bis(1,1-dimethylethyl)-4-mercaptophenol in acetonitrile under argon. Triethylamine is added to the solution with stirring at room temperature under argon for about 12 hours. The solution is acidified with 10% hydrochloric acid with stirring. It is extracted with ethyl acetate, the extracts combined, washed with water and dried over sodium sulfate. The solvent is removed on a rotary evaporator and the product is purified by chromatography on silica.

The active agents of this invention can be administered to animals, including humans and other mammals, as pure compounds. Thus the word animals is used in its broadest sense. However, it is advisable to first combine one or more of the active compounds with one or more suitable pharmaceutically acceptable carriers or diluents to attain a satisfactory size to dosage relationship and thereby obtain a pharmaceutical composition.

Pharmaceutical carriers which are liquid or solid can be employed. Solid carriers such as starch, sugars, talc and the like can be used to form powders which may be used for direct administration or to fill gelatin capsules. Suitable lubricants such as magnesium stearate, stearic acid, as well as binders and disintegrating agents may be included to form tablets. Additionally, flavoring and sweetening agents may be added.

Unit dosage forms such as tablets and capsules can contain any suitable, predetermined, therapeutically effective amount of one or more active agents and a pharmaceutically acceptable carrier or diluent. Generally speaking, solid oral unit dosage forms of a compound of this invention will contain from 1.75 to 750 mg per tablet of drug.

The compounds of this invention exhibit both oral and parenteral activity and accordingly can be formulated in dosage forms for either oral or parenteral administration.

Solid oral dosage forms include capsules, tablets, pills, powders, granules and the like.

Liquid dosage forms for oral administration include emulsions, suspensions, solutions, syrups and the like containing diluents commonly used in the art such as water. Besides inert diluents, such preparations can also include adjuvants such as wetting agents, emulsifying and suspending agents, and sweetening, flavoring and perfuming agents.

Preparations for parenteral administration include sterile aqueous or non-aqueous solutions. Examples of nonaqueous solvents or vehicles are propylene glycol, polyethylene glycol, vegetable oils such as olive oil and injectable organic esters such as ethyl oleate. The parenteral preparations are sterilized by conventional methods.

The compounds of this invention may also be formulated for topical or transdermal application using carriers which are well known in the art, as well as in aerosols or sprays for nasal administration.

The amount of active ingredient administered may be varied; however, it is necessary that the amount of active ingredient be such that a suitable dosage is given. The selected dosage depends upon the desired therapeutic effect, the route of administration and the duration of treatment. Generally speaking, oral dosages of from 0.1 to 200 mg/kg, and preferably from 0.5 to 50 mg/kg of body weight daily are administered to patients in need of such treatment, preferably in divided dosages, e.g. three to four times daily. The compounds may also be applied topically when appropriate.

A typical tablet of this invention can have the following composition:

| Ingredient | Mg/tablet |
| --- | --- |
| Active ingredient | 100 |
| Starch, U.S.P. | 57 |
| Lactose, U.S.P. | 73 |
| Talc, U.S.P. | 9 |
| Stearic acid | 12 |

It will be understood by those skilled in the art that the above examples are illustrative, not exhaustive, and that modifications may be made without departing from the spirit of the invention and the scope of the claims.

What is claimed is:

1. A method of inhibiting invasive activity and related metastasis of tumor cells in a mammal without treating the tumor cells comprising administering an amount of a compound of the formula

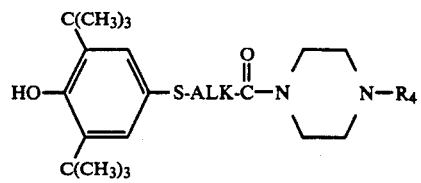

wherein Alk is straight or branched chain lower alkylene and $R_4$ is selected from the group consisting of hydrogen, lower alkyl, phenyl, or benzyl; or a pharmaceutically acceptable salt thereof, which is effective to inhibit tumor cell invasive activity and related metastasis to a mammal having tumor cells sensitive to said compound.

2. A method according to claim 1 wherein Alk is ethylene.

3. A method according to claim 1, wherein said compound is 1-[3-[[3,5-bis(1,1-dimethylethyl)-4-hydroxyphenyl]-thio]-1-oxopropyl]-4-methylpiperazine or a pharmaceutically acceptable salt thereof.

4. A method according to claim 1, wherein said compound is 1-[3-[[3,5-bis(1,1-dimethylethyl)-4-hydroxyphenyl]-thio]-1-oxopropyl]-4-methylpiperazine monohydrochloride.

5. A method according to claim 1, wherein said compound is 1-[3-[[3,5-bis(1,1-dimethylethyl)-4-hydroxyphenyl]-thio]-1-oxopropyl]-4-(phenylmethyl)piperazine or a pharmaceutically acceptable salt thereof.

6. A method according to claim 1, wherein said compound is 1-[3-[[3,5-bis(1,1-dimethylethyl)-4-hydroxyphenyl]-thio]-1-oxopropyl]-4-(phenylmethyl)piperazine monohydrochloride.

* * * * *

UNITED STATES PATENT AND TRADEMARK OFFICE
CERTIFICATE OF CORRECTION

PATENT NO. : 5,010,080

DATED : Apr. 23, 1991

INVENTOR(S) : Fuller, et. al.

It is certified that error appears in the above-identified patent and that said Letters Patent is hereby corrected as shown below:

Column 11, line 67, reading "Cald.:" should read -- Calc.: --.

Column 12, line 35, reading "Calc C," should read -- Calc.: C, --.

Column 12, line 68, reading "Calc. C," should read -- Calc.: C, --.

Column 15, line 15, reading "Calc. C," should read -- Calc.: C, --.

Signed and Sealed this

Ninth Day of February, 1993

Attest:

STEPHEN G. KUNIN

*Attesting Officer*     *Acting Commissioner of Patents and Trademarks*